United States Patent [19]

Stenzel et al.

[11] Patent Number: 4,631,281
[45] Date of Patent: Dec. 23, 1986

[54] SUBSTITUTED PHENYLPIPERAZINYL-PROPANOLS, A PROCESS FOR THEIR PREPARATION AND THEIR USE, AND FORMULATIONS CONTAINING THESE COMPOUNDS

[75] Inventors: Wolfgang Stenzel, Reinbek; Eva Hofferber, Hamburg, both of Fed. Rep. of Germany

[73] Assignee: Beiersdorf Aktiengesellschaft, Hamburg, Fed. Rep. of Germany

[21] Appl. No.: 750,729

[22] Filed: Jun. 28, 1985

[30] Foreign Application Priority Data

Jul. 5, 1984 [DE] Fed. Rep. of Germany ....... 3424685

[51] Int. Cl.$^4$ .................... A61K 31/445; C07D 401/10
[52] U.S. Cl. ..................................... 514/252; 544/360
[58] Field of Search ......................... 544/360; 514/252

[56] References Cited

U.S. PATENT DOCUMENTS 3,941,789  3/1976  Renth .................................. 544/360

FOREIGN PATENT DOCUMENTS

| 0089634 | 9/1983 | European Pat. Off. ............ 544/360 |
| 2337461 | 2/1975 | Fed. Rep. of Germany . |
| 2824764 | 12/1979 | Fed. Rep. of Germany . |
| 2824677 | 12/1979 | Fed. Rep. of Germany . |
| 2925448 | 1/1980 | Fed. Rep. of Germany . |
| 2834114 | 2/1980 | Fed. Rep. of Germany . |
| 2853996 | 7/1980 | Fed. Rep. of Germany . |
| 3200304 | 8/1982 | Fed. Rep. of Germany . |
| 3226863 | 4/1983 | Fed. Rep. of Germany . |
| 3326148-A1 | 6/1984 | Fed. Rep. of Germany . |

OTHER PUBLICATIONS

Journal of Medicinal Chemistry, 1974, vol. 17, No. 5, pp. 529–533.

*Primary Examiner*—Sidney Marantz
*Assistant Examiner*—Robert Benson
*Attorney, Agent, or Firm*—Sprung Horn Kramer & Woods

[57] ABSTRACT

Substituted phenylpiperazinyl-propanols of the formula I

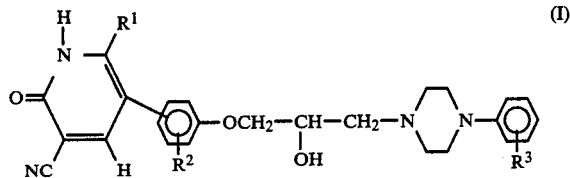

in which $R^1$ denotes hydrogen or an alkyl group with 1 to 4 carbon atoms and $R^2$ and $R^3$, which can be identical or different, each denote hydrogen, halogen, cyano, a trifluoromethyl group, a nitro group, a hydroxyl group, an alkoxy group or an alkyl group with in each case 1 to 4 carbon atoms, it being possible for the alkyl parts in each case to be straight-chain or branched, and their tautomeric forms and their salts as well as acid addition salts and N-oxides, have useful pharmacological properties, in particular a positively inotropic, vasodilating, broncholytic and platelet aggregation-inhibiting action and are therefore suitable for the treatment of cardiac insufficiency, hypertension, asthma and thrombosis.

12 Claims, No Drawings

SUBSTITUTED PHENYLPIPERAZINYL-PROPANOLS, A PROCESS FOR THEIR PREPARATION AND THEIR USE, AND FORMULATIONS CONTAINING THESE COMPOUNDS

The invention relates to new substituted phenyl-piperazinyl-propanols of the formula I

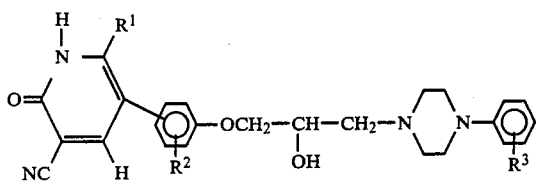

in which $R^1$ denotes hydrogen or an alkyl group with 1 to 4 carbon atoms and $R^2$ and $R^3$, which can be identical or different, each denote hydrogen, halogen, cyano, a trifluoromethyl group, a nitro group, a hydroxyl group, an alkoxy group or an alkyl group with in each case 1 to 4 carbon atoms, it being possible for the alkyl parts in each case to be straight-chain or branched, and their tautomeric forms and their salts as well as acid addition salts and N-oxides, a process for their preparation and their use, and formulations containing these compounds.

For simplicity, the compounds according to the invention are defined in only one tautomeric form represented by formula I. However, the invention extends to all the tautomeric forms of the compounds.

Although pharmaceutically acceptable salts and acid addition salts of the new compounds of the formula I and tautomeric forms and N-oxides thereof are preferred, all the salts lie within the scope of the invention. All the salts are useful for the preparation of the compounds, even if the particular salt is desired only as an intermediate, such as, for example, if the salt is formed only for the purpose of purification or identification, or if it is used as an intermediate in the preparation of a pharmaceutically acceptable salt, for example by ion exchange procedures.

The compounds of the general formula I and salts thereof contain asymmetric carbon atoms. The invention thus also relates to the various optical isomers and the diastereoisomers, as well as to the salts and addition salts of these compounds with acids. The racemates can be resolved into their optical antipodes by methods which are known per se.

The invention also relates to the N-oxides of the compounds of the general formula I. They are obtainable by known preparation processes (H. S. Mosher et al., Org. Synth., Coll. Vol. IV, 828, 1963).

Particularly preferred alkyl groups are the methyl group and the ethyl group. Halogen is preferably fluorine or chlorine. Preferred alkoxy groups are methoxy and ethoxy groups.

The pyridinone radical is preferably located in the 4-position of the phenyl nucleus.

The following compounds of the general formula I, N-oxides thereof and salts thereof are preferred: 1-[4-(3-cyano-1,2-dihydro-2-oxo-pyridin-5-yl)-phenoxy]-3-[4-(2-methoxyphenyl)-piperazin-1-yl]-propan-2-ol, 1-[3-(3-cyano-1,2-dihydro-6-methyl-2-oxo-pyridin-5-yl)-phenoxy]-3-[4-(2-methoxyphenyl)-piperazin-1-yl]-propan-2-ol, 1-[4-(3-cyano-1,2-dihydro-6-methyl-2-oxo-pyridin-5-yl)-phenoxy]-3-[4-methylphenyl)-piperazin-1-yl]-propan-2-ol, 1-[4-(3-cyano-1,2-dihydro-6-methyl-2-oxo-pyridin-5-yl)-2-methoxyphenoxy]-3-[4-(2-methoxyphenyl)-piperazin-1-yl]-propan-2-ol, 1-[4-(3-cyano-1,2-dihydro-6-methyl-2-oxo-pyridin-5-yl)phenoxy]-3-[4-(3-methoxyphenyl)-piperazin-1-yl]-propan-2ol, 1-[4-(3-cyano-1,2-dihydro-6-methyl-2-oxo-pyridin-5-yl)-2-methoxyphenoxy]-3-[4-(2-methylphenyl)-piperazin-1yl]propan-2-ol, 1-[4-(3-cyano-1,2-dihydro-6-methyl-2-oxopyridin-5-yl)-phenoxy]-3-(4-phenylpiperazin-1-yl)-propan-2-ol, 1-[3-(3-cyano-1,2-dihydro-6-methyl-2-oxo-pyridin-5-yl)-phenoxy]-3-(4-phenylpiperazin-1-yl)-propan-2-ol hydrochloride, 1-[2-(3-cyano-1,2-dihydro-6-methyl-2-oxo-pyridin-5-yl)-phenoxy]-3-(4-phenylpiperazin-1-yl)-propan-2-ol, 1-[4-(3-cyano-1,2-dihydro-6-methyl-2-oxo-pyridin-5-yl)phenoxy]-3-[4-(4-hydroxyphenyl)-piperazin-1-yl]-propan-2-ol and 1-[4-(3-cyano-1,2-dihydro-6-ethyl-2-oxo-pyridin5-yl)- phenoxy]-3-[4-(2-methoxyphenyl)-piperazin-1-yl]-propan-2-ol.

The following compounds of the general formula I, N-oxides thereof and salts thereof with a high therapeutic value are particularly preferred, and in particular in the form of the racemate and in the form of the optically active isomers: 1-[4-(3-cyano-1,2-dihydro-6-methyl-2-oxopyridin-5-yl)-phenoxy]-3-[4-(2-methoxyphenyl)-piperazin1-yl]-propan-2-ol, 1-[4-(3-cyano-1,2-dihydro-6-methyl-2-oxo- pyridin-5-yl)-phenoxy]-3-[4-(2-methylphenyl)-piperazin-1-yl]-propan-2-ol, 1-[4-(3-cyano-1,2-dihydro-6 -methyl-2oxo-pyridin-5-yl)-2-methoxyphenoxy]-3-[4-(2-methoxyphenyl)-piperazin-1-yl]-propan-2-ol and 1-[4-(3-cyano-1,2-dihydro-6-methyl-2oxo-pyridin-5-yl)-phenoxy]-3-(4-phenylpiperazin-1-yl)-propan-2-ol.

The compounds of the formula I according to the invention and their physiologically acceptable salts and acid addition salts and N-oxides are therapeutic active compounds, have a powerful pharmacological action and are useful medicaments. In particular, they exhibit a positively inotropic, vasodilating, broncholytic and platelet aggregation-inhibiting action and are suitable for the treatment of cardiac insufficiency, hypertension, asthma and thrombosis.

The compounds of the present invention can be administered orally or parenterally to humans in a dosage of 1–800 mg, preferably 10–200 mg and particularly preferably 20–100 mg per day, especially in divided doses, for example three times daily. These dosages are advantageous for the treatment of the abovementioned diseases, in particular cardiac insufficiency and/or hypertension.

The positively inotropic action of the compounds according to the invention was determined on the papillary muscle of guinea pigs (Naunyn-Schmiedeberg's Arch. Pharmacol. 304, 37, 1978). The concentration of the substance in the organ bath was in each case $10^{-4}$ mole/l. The maximum percentage increase in the contraction amplitude was in each case determined on three papillary muscles and was at least 50%.

According to the invention, pharmaceutical compositions which contain compounds of the formula I or their N-oxides or their pharmaceutically acceptable salts, together with pharmaceutically acceptable diluents or excipients are provided.

The compounds according to the invention can be mixed with the customary pharmaceutically acceptable diluents or excipients and, if appropriate, with other auxiliaries, and can be administered, for example, orally or parenterally. They can be administered orally in the form of tablets, coated tablets, syrups, suspensions and liquids, or parenterally in the form of solutions or suspensions. Products to be administered orally can contain one or more additives, such as sweeteners, aromatising agents, colouring agents and preservatives. Tablets can contain the active compound mixed with customary pharmaceutically acceptable auxiliaries, for example inert diluents, such as calcium carbonate, sodium carbonate, lactose and talc, granulating agents and agents which promote disintegration of the tablets on oral administration, such as starch or alginic acid, binders, such as starch or gelatin, and lubricants, such as magnesium stearate, stearic acid and talc.

Examples of suitable excipients are milk sugar (lactose), gelatin, maize starch, stearic acid, ethanol, propylene glycol, ethers of tetrahydrofuryl alcohol and water.

The tablets can be coated by known procedures in order to delay disintegration and absorption in the gastrointestinal tract, which means that the activity of the active compound can extend over a longer period of time. In the suspensions, the active compound can likewise be mixed with auxiliaries which are usual for the preparation of such compositions, for example suspending agents, such as methyl cellulose, tragacanth or sodium alginate, wetting agents, such as lecithin, polyethylene stearate and polyoxyethylene sorbitan monooleate, and preservatives, such as ethyl parahydroxybenzoate. Capsules can contain the active compound as the sole constituent or mixed with a solid diluent, such as calcium carbonate, calcium phosphate or kaolin. The injectable products are likewise formulated in a manner which is known per se. The pharmaceutical products can contain the active compound in an amount of 0.1 to 90%, in particular 1 to 90%, the remainder being an excipient or additive. Solid products, such as tablets and capsules, are preferred in respect of preparation and administration. The products preferably contain the active compound in an amount of 5-40 mg.

The new compounds of the general formula I can be prepared by reacting compounds of the formula II

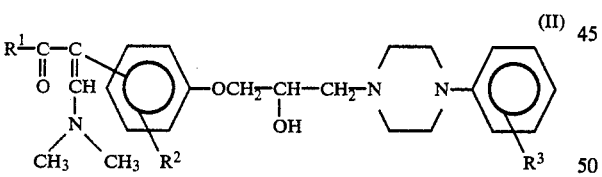

in which $R^1$, $R^2$ and $R^3$ have the meanings given for formula I, with cyanoacetamide.

The reaction of the compounds of the formula II with cyanoacetamide is preferably carried out by heating in a suitable solvent, for example in a lower alcohol, such as methanol or ethanol, or an aprotic solvent, such as dimethylformamide, tetrahydrofuran, acetonitrile, diethyl ether or toluene, in the presence of a basic condensing agent, preferably an alkali metal alcoholate, alkali metal carbonate or alkali metal hydride. The use of sodium carbonate in the presence of a phase transfer catalyst, preferably tetrabutylammonium disulphate, has proved particularly suitable. The preferred solvent in this process is acetonitrile. The reaction temperatures are between room temperature and 150° C., preferably between 50° and 100° C. The reaction times vary between 8 and 72 hours. The optimum reaction times are advantageously determined by thin layer chromatography on silica gel.

The compounds of the formula II in which $R^1$, $R^2$ and $R^3$ have the meanings given for formula I can be prepared by reaction of aryl ketones of the formula III

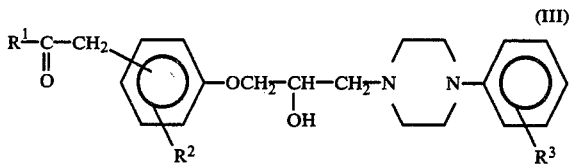

in which $R^1$, $R^2$ and $R^3$ have the meaning given, with dimethylformamidedimethylacetal. The reactions can be carried out in a solvent, such as dimethylformamide, methanol or ethanol, at temperatures between 50° C. and the boiling point of the reaction mixture, preferably between 60° and 100° C.

If the reaction is carried out without a solvent using an excess of dimethylformamidedimethylacetal, the reaction times are between 1 and 8 hours.

The compounds of the formula III can be prepared from compounds of the formula Iva and Ivb and mixtures thereof

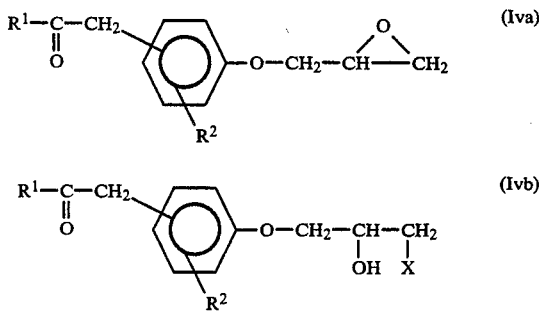

in which $R^1$ and $R^2$ have the meanings given in formula I and X is halogen, preferably chlorine or bromine, with a piperazine derivative of the formula V

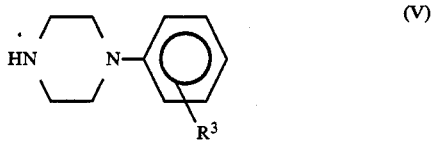

in which $R^3$ has the meanings given in formula I. The reactions are preferably carried out in a solvent at temperatures between 20° and 120° C., advantageously at 50°–120° C.

The solvents used are preferably lower alcohols with 1 to 4 carbon atoms, in particular ethanol or isopropanol. However, the reactions can also be carried out in ethers, such as diethyl ether, tetrahydrofuran or dioxane, dimethylformamide or dimethylsulphoxide. The reaction time depends on the reaction temperature and is in general 2 to 15 hours.

The compounds of the formula IV in which $R^1$ and $R^2$ have the meanings given in formula I can be prepared by alkylation of phenols of the general formula VI

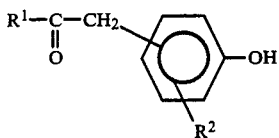

in which R¹ and R² have the meanings given for formula I, with an epihalogenohydrin, such as epichlorohydrin or epibromohydrin.

The alkylations of the phenol derivatives of the formula VI are advantageously carried out at temperatures of 0°–120° C. in an inert solvent, such as acetone, a lower alcohol with 1 to 4 carbon atoms, such as methanol, ethanol, propanol or butanol, an ether, such as diethyl ether, tetrahydrofuran or dioxane, or dimethylformamide or dimethylsulphoxide, or in excess alkylating agent as the solvent. The reactions are preferably carried out in the presence of a base as an acid-binding agent. Suitable bases are alkali metal carbonates, bicarbonates, hydrides or hydroxides, in particular of sodium and potassium. Preferably, the phenol derivatives are reacted with epichlorohydrin in dimethylsulphoxide in the presence of sodium hydroxide solution at room temperature or temperatures up to 50° C.

The starting materials used are known or can be prepared by processes which are known per se or by processes analogous to those described here or analogous to processes which are known per se.

The compounds of the general formula I can be either bases or acids, or can be amphoteric, and are therefore isolated from the reaction mixtures in the form of their salts or acid addition salts. As bases, they can be converted into salts with suitable inorganic or organic acids by known processes, or as acids they can form salts with bases.

Physiologically acceptable salts or acid addition salts are preferred. Examples of inorganic acids which are suitable for this purpose are hydrogen halide acids, for example hydrochloric acid or sulphuric acid, and examples of suitable organic acids are fumaric acid, maleic acid, citric acid and tartaric acid. For the preparation, an alcoholic solution of a suitable acid is added to the hot alcoholic solution of the base and, after adding ether, the salt is obtained. Preferred salts are the alkali metal, alkaline earth metal and ammonium salts of the compounds of the formula I, which are obtained with the corresponding bases, in particular sodium hydroxide, potassium hydroxide or ammonium hydroxide.

The compounds of the formula I according to the invention have a chirality centre on carbon atom 2 of the isopropanol chain and, depending on the substituents, may have further asymmetric carbon atoms and can therefore exist as racemates and diastereoisomers. Diastereoisomers can be resolved into their racemic modifications in a known manner on the basis of the physicochemical differences of their constituents. Racemates can be resolved by known methods, for example by recrystallisation from optically active solvents, by microorganisms or by reaction with an optically active acid or base which forms a salt with the racemic compound, resolution of the diastereoisomers by fractional crystallisation and liberation of the enantiomers by suitable agents. Examples of particularly suitable optically active acids are the d- and l-forms of tartaric acid, ditoloyltartaric acid, malic acid, mandelic acid, camphorsulphonic acid or pyrrolidone-carboxylic acid. Suitable optically active bases are -phenylethylamine, menthylamine, ephedrine, brucine and quinine. The more active of the antipodes is advantageously isolated. According to the invention, however, it is also possible to obtain the pure enantiomers by asymmetric synthesis.

The following Examples illustrate the invention:

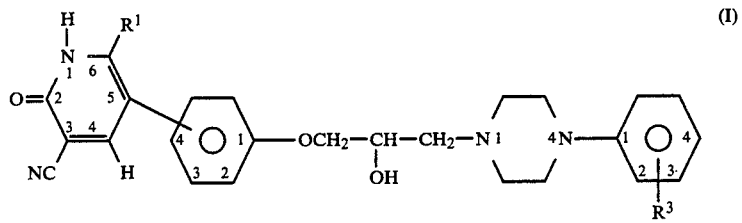

EXAMPLE 1

1-[4-(3-Cyano-1,2-dihydro-6-methyl-2-oxo-pyridin-5-yl)-phenoxy]-3-[4-(2-methoxyphenyl)-piperazin-1-yl]-propan-2-ol (a) 32.8 g of 4-hydroxyphenylacetone are dissolved in 175 g of 5% strength sodium hydroxide solution, with cooling, and 60 ml of dimethylsulphoxide are added. 35 ml of epichlorohydrin are then added dropwise at temperatures below 20° C. The batch is left to stand overnight and is extracted with chloroform, the extract is washed with water and dried with calcium chloride and the solvent is removed under a water pump vacuum. The residue is distilled under an oil pump under 0.2 mbar.

Boiling point: 139°–141° C. 33.2 g of 4-(2,3-epoxypropoxy)-phenylacetone are obtained.

Melting point: 43° C.

(b) 30.0 g of 4-(2,3-epoxypropoxy)-phenylacetone and 25.6 g of 2-methoxyphenyl-piperazine are heated under reflux in 300 ml of ethanol for 3 hours. The solvent is then distilled off. The residue is made to crystallise with ethyl acetate/hexane. 32.5 g of 1-[4-(propan-2-on-yl)-phenoxy]-3-[4-(2-methoxyphenyl)-piperazin-1-yl]-propan-2-ol are obtained.

Melting point: 42°–43° C.

(c) 32.0 g of 1-[4-propan-2-on-yl)-phenoxy]-3-[4(2-methoxyphenyl)-piperazin-1-yl]-propan-2-ol are dissolved in 100 ml of methanol, 20.0 ml of dimethylformamidedimethylacetal are added and the mixture is heated under reflux overnight. The solvent is then distilled off in vacuo and the residue is triturated with petroleum ether and made to crystallise with ether at −60° C. 28.5 g of 1-[4-(4-dimethylamino-3-buten-2-on-3-yl)-phenoxy]-4-[4-(2-methoxyphenyl)-piperazin-1-yl]propan-2-ol are obtained.

Melting point 185° C.

(d) 9.0 g of 1-[4-(4-dimethylamino-3-buten-2-on-3-yl)-phenoxy]-3-[4-(2-methoxyphenyl)-piperazin-1-yl]-propan2-ol are heated under reflux in 100 ml of acetonitrile with 5.66 g of potassium carbonate, 0.67 g of tetrabutylammonium bisulphate and 2.52 g of cyanoacetamide for 36 hours. The solvent is then distilled off in vacuo, the residue is dissolved in 50 ml of water and the solution is neutralised with dilute hydrochloric acid and extracted several times with ethyl acetate. The extracts are dried and concentrated. The residue is purified by column chromatography on silica gel (chloroform:methanol=10:1). 2.2 g of 1-[4-(3-cyano-1,2-dihydro-6-methyl-2-oxo-pyridin-5-yl)-penoxy]-3-[4-(2-methoxyphenyl)-piperazin-1-yl]-propan-2-ol are obtained.

Melting point 159°–160° C.

(e) 2.0 g of this product are suspended in 20 ml of absolute methanol. Ethereal HCl is added dropwise, with cooling, until the pH reaches 3, and 200 ml of ether are then added, the mixture is cooled to 0° C. for some hours and the precipitate is filtered off with suction. 2.1 g of 1-[4-(3-cyano-1,2-dihydro-6-methyl-2-oxo-pyridin-5-yl)-phenoxy]-3-[4-(2-methoxyphenyl)-piperazin-1-yl]-propan-2-ol hydrochloride are obtained.

Melting point 298° C.

EXAMPLE 2

1-[4-(3-Cyano-1,2-dihydro-6-methyl-2-oxo-pyridin-5-yl)-phenoxy]-3-[4-phenyl-piperazin-1-yl]-propan-2-ol (a) 10.0 g of 4-(2,3-epoxypropoxy)phenylacetone are dissolved in 60 ml of acetone and the solution is heated under reflux with 7.64 g of phenylpiperazine for 3 hours. The mixture is allowed to cool and the product which has crystallised out is filtered off with suction. 16.05 g of 1-[4-(propan-2-on-yl)-phenoxy]-3-(4-phenyl-piperazin-1-yl)-propan-2-ol are obtained.

Melting point 121°–122° C.

(b) 14.0 g of 1-[4-propan-2-on-yl)-phenoxy]-3-(4-phenylpiperazin-1-yl)-propan-2-ol and 18 ml of dimethylformamidedimethylacetal are dissolved in 60 ml of methanol and the solution is heated under reflux for 5 hours. It is allowed to cool, the product is filtered off with suction and the residue is triturated with ether. 13.1 g of 1-[4-(4-dimethylamino-3-buten-2-on-3-yl)-phenoxy]-4-(4-phenylpiperazin-1-yl)-propan-2-ol are obtained.

Melting point 153°–154° C.

(c) 1.93 g of cyanoacetamide and 10.0 g of 1-[4-(4-dimethylamino-3-buten-2-on-3-yl-phenoxy]-3-(phenyl-piperazin-1-yl)-propan-2-ol are added to a solution of 3.0 g of sodium ethylate in 130 ml of ethanol and the mixture is heated under reflux for 40 hours. It is allowed to cool and the crystals are filtered off with suction and washed with water and ethanol. The hydrochloride is pre-cipitated analogously to Example 1(e) and 5.95 g of 1-[4-(3-cyano-1,2-dihydro-6-methyl-2-oxo-pyridin-5-yl)-phenoxy]-3-[4-phenyl-piperazin-1-yl]-propan-2-ol hydrochloride hydrate are obtained.

Melting point 206°–207° C.

EXAMPLE 3

1-[4-(3-Cyano-1,2-dihydro-6-methyl-2-oxo-pyridin-5-yl)-phenoxy]-3-[4-(2-methylphenyl)-piperazin-1-yl]-propan-2-ol (a) 4-(2,3-Epoxypropoxy)-phenylacetone is reacted with 2-methylphenyl-piperazine analogously to Example 2(a). 1-[4-(propan-2-on-yl)-phenoxy]-3-[4-(2-methylphenyl)-piperazin-1-yl]-propan-2-ol is obtained.

Melting point 232° C.

(b) This product is reacted with dimethylformamidedimethylacetal analogously to Example 2(b). 1-[4-(dimethylaminomethylamino- 3-buten-2-on-3-yl)-phenoxy]-3-[4-(2-methylphenyl)-piperazin-1-yl]-propan-2-ol is obtained.

Melting point 234°–236° C.

(c) Reaction of this substance with cyanoacetamide analogously to 1(d) and conversion of the reaction product into the hydrochloride analogously to 1(e) gives 1-[4-(3-cyano-1,2-dihydro-6-methyl-2-oxo-pyridin-5-yl)-phenoxy]-3-[4-(2-methylphenyl)-piperazin-1-yl]-propan-2-ol hydrochloride.

Melting point 292° C.

EXAMPLE 4

1-[2-Methoxy-4-(3-cyano-1,2-dihydro-6-methyl-2-oxo-pyridin-5-yl)-phenoxy]-3-[4-(2-methoxyphenyl)-piperazin-1-yl]-propan-2-ol (a) 4-(2,3-Epoxypropoxy)-2-methoxyphenylacetone is reacted with 2-methoxyphenyl-piperazine analogously to Example 2(a). 1-[2-Methoxy-4-(propan-2-on-yl)-phenoxy]-3[4-(2-methylphenyl)-piperazin-1-yl]-propan-2-ol is obtained.

Melting point 128° C.

(b) After reaction of this compound with dimethylformamidedimethylacetal analogously to 2(b), 1-[4-(4-dimethylamino-3-buten-2-on-3-yl)-2-methoxy-phenoxy]-3-[4-(2-methylphenyl)-piperazin-1-yl]-propan-2-ol is obtained.

Melting point 95° C.

(c) 1-[2-Methoxy-4-(3-cyano-1,2-dihydro-6-methyl-2-oxo-pyridin-5-yl)-phenoxy]-3-[4-(2-methoxyphenyl)-piperazin-1-yl]-propan-2-ol dihydrochloride is obtained from this compound by reaction with cyanoacetamide analogously to 1(d) and subsequent hydrochloride precipitation analogously to 1(e).

Melting point 176°–178° C.

EXAMPLE 5

1-[3-(3-Cyano-1,2-dihydro-6-methyl-2-oxo-pyridin-5-yl)-phenoxy]-3-[4-(2-methoxyphenyl)-piperazin-1-yl]-propan-2-ol (a) 3-(2,3-Epoxypropoxy)-phenylacetone is reacted with 2-methoxyphenylpiperazine analogously to Example 2(a). 1-[3-(Propan-2-on-yl)-phenoxy]-3-[4-(2-methoxyphenyl)-piperazin-1-yl]-propan-2-ol is obtained as a syrupy product.

(b) Reaction of this compound with dimethylformamideimethylacetal analogously to Example 2(b) gives 1-[3-(4-dimethylamino-3-buten-2-on-3-yl)-phenoxy]-3-[4-(2-methoxyphenyl)-piperazine-1-yl]-propan-2-ol as a syrupy product.

(c) 1-[3-(3-Cyano-1,2-dihydro-6-methyl-2-oxo-pyridin-5-yl)-phenoxy]-3-[4-(2methoxyphenyl)-piperazine-1-yl]-propan-2-ol dihydrochloride is obtained from this compound by reaction with cyanoacetamide analogously to Example 1(d) and hydrochloride precipitation analogously to Example 1(c).

Melting point 174°–175° C.

The compounds of the formula I according to the invention which are listed in the following Table and in which the pyridinone ring is in the 4-position are obtained analogously to the above Examples:

| Example | $R^1$ | $R^2$ | $R^3$ | Salt | Melting point °C. |
|---|---|---|---|---|---|
| 6 | $CH_3$ | H | 3-$OCH_3$ | dihydrochloride hydrate | 239 |
| 7 | $CH_3$ | H | 4-OH | hydrochloride | 262 |

-continued

| Example | R¹ | R² | R³ | Salt | Melting point °C. |
|---|---|---|---|---|---|
| 8 | CH₃ | H | 2-F | hydrochloride | 253–254 |
| 9 | CH₃ | H | 2-Cl | hydrochloride hydrate | 298–299 |
| 10 | CH₃ | 3-OCH₃ | 2-OCH₃ | hydrochloride | 234 |
| 11 | CH₃ | H | 2-CF₃ | dihydrochloride hydrate | 246–247 |
| 12 | CH₃ | H | 2-NO₂ | hydrochloride | 259 |
| 13 | CH₃ | H | 4-NO₂ | hydrochloride hydrate | 258–259 |
| 14 | CH₃ | H | 2-OC₂H₅ | hydrochloride hydrate | 230 |
| 15 | CH₃ | H | 3-CF₃ | dihydrochloride hydrate | 246–247 |
| 16 | CH₃ | H | 3-Cl | hydrochloride | 284–285 |
| 17 | CH₃ | H | 4-F | hydrochloride hydrate | 251–252 |
| 18 | CH₃ | H | 2-C₂H₅ | hydrochloride hydrate | 263–264 |
| 19 | CH₃ | H | 2-OH | hydrochloride hydrate | 283–284 |
| 20 | CH₃ | H | 2-Br | hydrochloride | 298 (decomp.) |
| 21 | CH₃ | H | 2-CN | hydrochloride | 157–158 |
| 22 | C₂H₅ | H | 2-OCH₃ | hydrochloride | 250 |
| 23 | CH₃ | H | 4-Cl | hydrochloride | 232 |

EXAMPLE 24

Preparation of tablets and capsules

Tablets and capsules containing the constituents shown below are prepared by known procedures. These are suitable for the treatment of the abovementioned diseases, in particular cardiac insufficiency, in dosage amounts of in each case one tablet or capsule three times daily.

| Constituents | Weight (mg) Tablet | Capsule |
|---|---|---|
| 1-[4-(3-Cyano-1,2-dihydro-6-methyl-2-oxo-pyridin-5-yl)-phenoxy]-3-[4-(2-methoxyphenyl)-piperazin-1-yl]-propan-2-ol hydrochloride | 10 | 10 |
| Tragacanth | 10 | — |
| Lactose | 247.5 | 300 |
| Maize starch | 25 | — |
| Talc | 15 | — |
| Magnesium stearate | 2.5 | — |

EXAMPLE 25

Preparation of ampoules

Ampoules which contain the constituents mentioned below can be prepared in a known manner. The active compound and sodium chloride are dissolved in water and glass ampoules are filled with the solution under nitrogen.

| | |
|---|---|
| 1-[4-(3-Cyano-1,2-dihydro-6-methyl-2-oxo-pyridin-5-yl)-phenoxy]-3-[4-(2-methoxyphenyl)-piperazin-1-yl]-propan-2-ol hydrochloride | 2 mg |
| Sodium chloride | 18 mg |
| Distilled water to | 2.0 ml |

We claim:

1. Substituted phenylpiperazinyl-propanols formula I

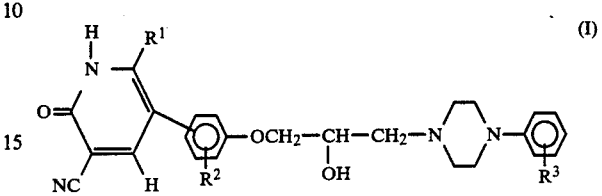

in which $R^1$ denotes hydrogen or an alkyl group with 1 to 4 carbon atoms and $R^2$ and $R^3$, which can be identical or different, each denote hydrogen, halogen, cyano, a trifluoromethyl group, a nitro group, a hydroxyl group, an alkoxy group or an alkyl group with in each case 1 to 4 carbon atoms, it being possible for the alkyl parts in each case to be straight-chain or branched, and their tautomeric forms and their salts as well as acid addition salts and N-oxides.

2. A compound of claim 1, which is 1-[4-(3-cyano-1,2-dihydro-6-methyl-2-oxo-pyridin-5-yl)-phenoxy]-3-[4-(2-methoxyphenyl)-piperazin-1-yl]-propan-2-ol.

3. A compound of claim 1, which is 1-[4-(3-cyano-1,2-dihydro-6-methyl-2-oxo-pyridin-5-yl)-phenoxy]-3-[4-(2-methylphenyl)-piperazin-1-yl]-propan-2-ol.

4. A compound of claim 1, which is 1-[4-(3-cyano-1,2-dihydro-6-methyl-2-oxo-pyridin-5-yl)-2-methoxyphenoxy]-3[4-(2-methoxyphenyl)-piperazin-1-yl]-propan-2-ol.

5. A compound of claim 1, which is 1-[4-(3-cyano-1,2-dihydro-6-methyl-2-oxo-pyridin-5-yl)-phenoxy]-3-(4-phenylpiperazin-1-yl)-propan-2-ol.

6. A pharmaceutical composition containing, as an active ingredient, a cardiovascular effective amount of a compound according to claim 1 in admixture with an inert pharmaceutical carrier.

7. A medicament in dosage unit form comprising a cardiovascular effective amount of a compound according to claim 1 and an inert pharmaceutical carrier.

8. A medicament of claim 7 in the form of tablets, pills, dragees, capsules, ampoules or suppositories.

9. A method of combatting cardiovascular irregularity in warm-blooded animals which comprises administering to the said animal a cardiovascular effective amount of an active compound according to claim 1 either alone or in admixture with a diluent or in the form of a medicament.

10. A method according to claim 9 in which the active compound is adminstered in an amount of 1 to 800 mg per day.

11. A method according to claim 10 wherein the dosage is 10 to 200 mg per day.

12. A method according to claim 10 wherein the dosage is 20 to 100 mg per day.

* * * * *